US008673015B2

(12) United States Patent
Maroney et al.

(10) Patent No.: US 8,673,015 B2
(45) Date of Patent: *Mar. 18, 2014

(54) CONCAVE RESURFACING PROSTHESIS

(75) Inventors: Brian John Maroney, Fort Wayne, IN (US); Gerald Ross Williams, Villanova, PA (US)

(73) Assignee: DePuy Synthes Products, LLC, Raynham, MA (US)

(*) Notice: Subject to any disclaimer, the term of this patent is extended or adjusted under 35 U.S.C. 154(b) by 811 days.

This patent is subject to a terminal disclaimer.

(21) Appl. No.: 12/563,417

(22) Filed: Sep. 21, 2009

(65) Prior Publication Data

US 2010/0070044 A1 Mar. 18, 2010

Related U.S. Application Data

(60) Continuation of application No. 12/005,205, filed on Dec. 26, 2007, now abandoned, which is a division of application No. 10/259,045, filed on Sep. 27, 2002, now Pat. No. 7,329,284.

(51) Int. Cl.
*A61F 2/40* (2006.01)
(52) U.S. Cl.
USPC ..................................... 623/19.13
(58) Field of Classification Search
USPC ............. 623/19.11–19.14; 606/86 R
See application file for complete search history.

(56) References Cited

U.S. PATENT DOCUMENTS 3,694,820 A * 10/1972 Scales et al. ............... 623/19.12
3,855,638 A 12/1974 Pilliar
4,261,062 A * 4/1981 Amstutz et al. ............ 623/19.13
5,437,677 A * 8/1995 Shearer et al. .................. 606/96
5,470,336 A 11/1995 Ling et al.
5,489,310 A * 2/1996 Mikhail .................... 623/19.11
5,593,448 A 1/1997 Dong
5,630,819 A 5/1997 Ashby et al.
5,665,090 A 9/1997 Rockwood et al.
5,800,551 A 9/1998 Williamson et al.
5,879,355 A 3/1999 Ullmark (Continued)

FOREIGN PATENT DOCUMENTS

DE 3630069 1/1988
EP 0610575 A2 8/1994

(Continued)

OTHER PUBLICATIONS

Japanese Office Action in corresponding Japanese patent application (i.e., JP 2009-024546), mailed Aug. 17, 2010, 3 pages.

(Continued)

*Primary Examiner* — Anu Ramana
(74) *Attorney, Agent, or Firm* — Maginot, Moore & Beck, LLP

(57) ABSTRACT

A glenoid component for use with a prosthetic humeral component for use in performing shoulder arthroplasty is provided. The glenoid component may be fitted at least partially into a cavity formed in the glenoid vault. The glenoid component includes a body having a stem portion for inserting at least partially into the cavity formed in the glenoid vault. The stem portion cooperates with the interior wall of the cavity formed in the glenoid vault. The body has a bearing portion for articulating cooperation with the prosthetic humeral component.

14 Claims, 19 Drawing Sheets

(56) References Cited

U.S. PATENT DOCUMENTS

| | | | |
|---|---|---|---|
| 6,214,050 B1 | 4/2001 | Huene | |
| 6,228,900 B1 | 5/2001 | Shen et al. | |
| 6,281,264 B1 | 8/2001 | Salovey et al. | |
| 6,379,386 B1 * | 4/2002 | Resch et al. | 623/19.13 |
| 6,451,057 B1 | 9/2002 | Chen et al. | |
| 6,458,136 B1 | 10/2002 | Allard et al. | |
| 6,783,548 B2 * | 8/2004 | Hyde, Jr. | 623/18.12 |
| 2002/0065518 A1 | 5/2002 | Naybour et al. | |
| 2002/0133153 A1 | 9/2002 | Hyde, Jr. | |
| 2003/0055507 A1 | 3/2003 | McDevitt et al. | |

FOREIGN PATENT DOCUMENTS

| | | |
|---|---|---|
| EP | 1064890 A1 | 1/2001 |
| EP | 1136046 A2 | 9/2001 |
| FR | 2653660 | 5/1991 |
| GB | 2297257 | 7/1996 |
| JP | 60156453 A | 8/1985 |
| JP | 62254749 A | 11/1987 |
| JP | 9276305 A | 10/1997 |
| JP | 2001293019 | 10/2001 |
| WO | 92/14423 A1 | 9/1992 |
| WO | 97/11651 A1 | 4/1997 |
| WO | 00/09044 A1 | 2/2000 |
| WO | 0117444 | 3/2001 |
| WO | 02/062272 | 8/2002 |

OTHER PUBLICATIONS

Japanese Office Action corresponding to Japanese patent application JP 2009-024546, mailed Feb. 1, 2011 (2 pages).
European Search Report in corresponding European patent application (i.e., EP 10 15 6807), dated Apr. 29, 2010 (3 pages.

* cited by examiner

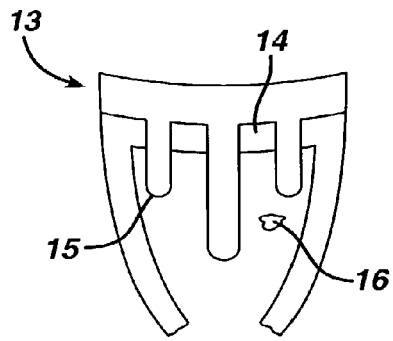 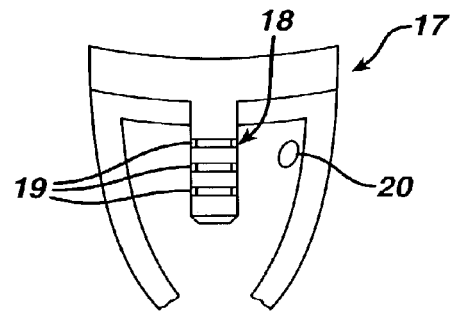
FIG. 6 PRIOR ART    FIG. 7 PRIOR ART
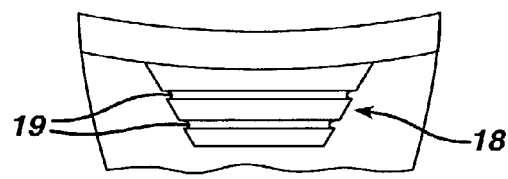
FIG. 7A PRIOR ART
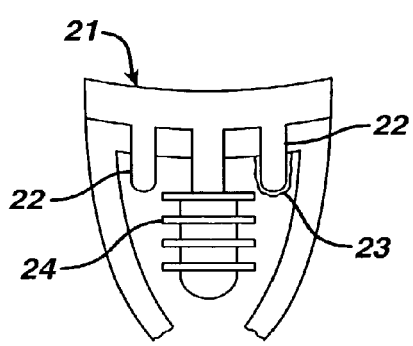 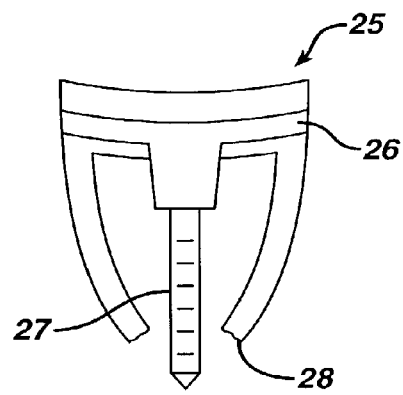
FIG. 8 PRIOR ART    FIG. 9 PRIOR ART

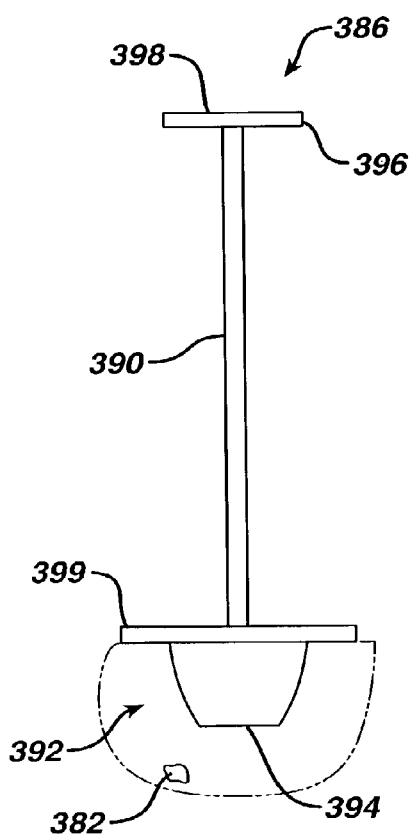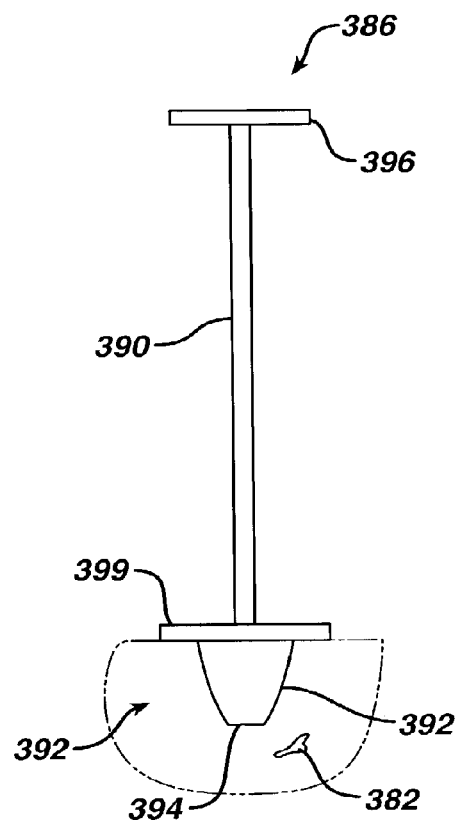
FIG. 16  FIG. 17

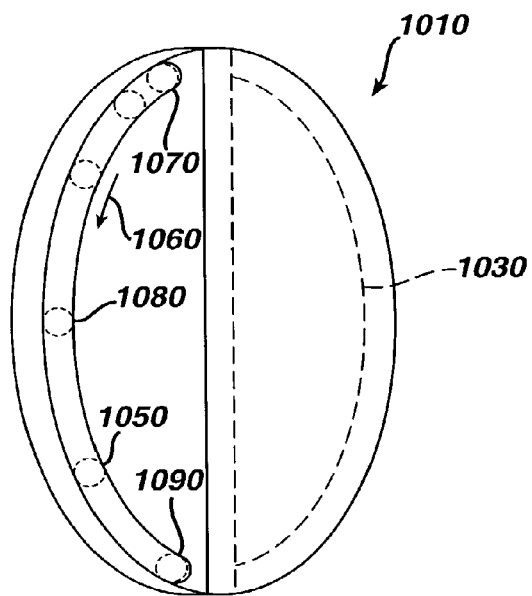
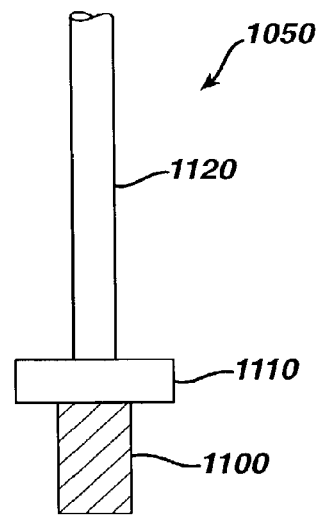
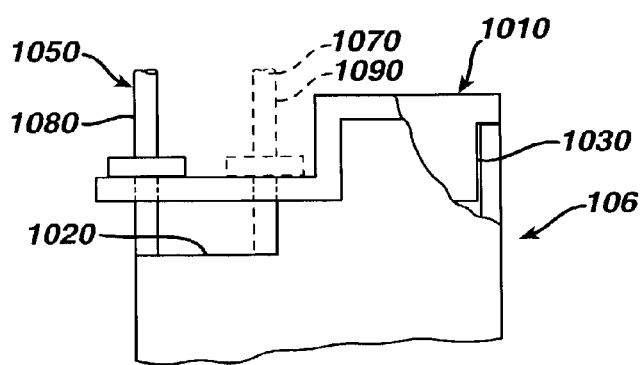

CONCAVE RESURFACING PROSTHESIS

This application is a Continuation Application of U.S. application Ser. No. 12/005,205, filed Dec. 26, 2007, and entitled Tamp for Concave Resurfacing Prosthesis (now Abandoned), which is a Divisional Application of U.S. application Ser. No. 10/259,045, filed Sep. 27, 2002, and entitled Concave Resurfacing Prosthesis (now U.S. Pat. No. 7,329,284 issued Feb. 12, 2008), the disclosures of each of which are hereby totally incorporated by reference in their entirety.

TECHNICAL FIELD

The present invention relates generally to the field of orthopaedics, and more particularly, to an implant for use in arthroplasty.

BACKGROUND

The invention relates to implantable articles and methods for manufacturing such articles. More particularly the invention relates to a bone prosthesis and a process for manufacturing the same.

There are known to exist many designs for and methods for manufacturing implantable articles, such as bone prostheses. Such bone prostheses include components of artificial joints, such as elbows, hips, knees, and shoulders. An important consideration in the design and manufacture of virtually any implantable bone prosthesis is that the prosthesis has adequate fixation when implanted within the body.

Earlier designs of implantable articles relied upon the use of cements such as polymethylmethacrylate (PMMA) to anchor the implant. The use of such cements can have some advantages, such as providing a fixation that does not develop free play or does not lead to erosion of the joining bone faces postoperatively. However, the current trend is to use the cements to a lesser extent because of their tendency to lose adhesive properties over time and the possibility that the cement contributes to wear debris within a joint.

Recently, implantable bone prostheses have been designed such that they encourage the growth of hard bone tissue around the implant. Such implants are often implanted without cement and the bone grows around surface irregularities for example, porous structures on the implant.

One such implantable prosthesis is a shoulder prosthesis. During the lifetime of a patient, it may be necessary to perform a total shoulder replacement procedure on a patient as a result of, for example disease or trauma, for example, disease from osteoarthritis or rheumatoid arthritis.

In a total shoulder replacement procedure, a humeral component having a head portion is utilized to replace the natural head portion of the arm bone or humerus. The humeral component typically has an elongated intermedullary stem which is utilized to secure the humeral component to the patient's humerus. In such a total shoulder replacement procedure, the natural glenoid surface of the scapula is resurfaced or otherwise replaced with a glenoid component that provides a bearing surface for the head portion of the humeral component.

Glenoid components have been designed which include a number of plastic inserts coupled to metal backings. The metal backings are provided to secure the plastic inserts to the glenoid surface of the scapula.

Unfortunately, for a variety of reasons, an implant, for example, a shoulder prosthesis, may occasionally need to be revised or have the old implant surgically removed and a new implant positioned where the prior implant had been removed. Such a procedure is called a revision surgery. In total shoulder arthroplasty, failure of the glenoid component is the primary cause for revision surgery. Primary failure modes are premature wear of the articulating surface and loss of fixation.

When a failed glenoid component is removed, often the subcondylar plate is damaged or missing along with a large defect in the cancellous bone of the glenoid vault of the scapula.

Fixation of a revision glenoid component can be difficult to achieve with a resulting limited bone stock remaining on the glenoid vault of the scapula after the revision surgery has been performed. Often the surgeon has to graft the glenoid defects and convert to a hemi-arthroplasty with a prosthetic humeral head articulating on the remaining natural glenoid articulating surface.

Attempts to provide for an adequate revision glenoid component for revision surgery have met with less than optimal results. For example, current glenoid prosthesis designs include pegged, finned, interference peg and metal back screw type of glenoid prosthesis.

Referring now to FIG. 1, a healthy glenoid fossa 1 which is a portion of the scapula is shown. The healthy glenoid fossa 1 includes a glenoid articulating surface 2 positioned on the subcondylar plate 3. The humeral head (not shown) of a healthy humerus rides against the glenoid articulating surface.

Referring now to FIG. 2, a glenoid 4 is shown with posterior erosion 5 on the glenoid articulating surface 6.

Prior art glenoid components have a generally concave shape with a cylindrical member or peg extending outwardly in a direction opposed to the concave articulating surface. When utilizing a standard glenoid prosthesis to repair a failed glenoid component, the posterior erosion requires that the subcondylar plate be resected or reduced. The subcondylar plate needs to be reamed or resected away to correct the version.

As shown in FIG. 3, the standard glenoid prosthesis 7 rests on only cortical bone 8 along the periphery of the glenoid articulating surface. Not only is the support at the cortical bone areas 8 very limited, the support between the cortical bone maybe full of voids 9 which further reduce the ability of the standard glenoid prosthesis to be properly supported.

Referring now to FIG. 4, a glenoid 10 is shown after removal of a failed glenoid component. The failed glenoid component resulted in a void in the subcondylar plate and the underlying cancellous bone bed.

Referring now to FIG. 5, the failed glenoid of FIG. 4 is shown with a standard glenoid prosthesis 11 positioned over the remaining portions 12 of the subcondylar plate. Again with the configuration of FIG. 5, the standard glenoid prosthesis is only supported at the remaining portions 12 of the subcondylar plate.

Referring now to FIGS. 6, 7, 8, and 9 various prior art attempts at providing a satisfactory glenoid prosthesis are shown.

Referring first to FIGS. 6 and 7, prosthesis 13 and 17 are shown, respectively, for use with PMMA cement.

Referring first to FIG. 6, standard glenoid prosthesis 13 is shown positioned over subcondylar plate 14. A series of pegs 15 are positioned through the subcondylar plate 14 into the cement 16 and cancellous bone bed. As can be seen, the prosthesis 13 requires an intact subcondylar plate 14 to properly support the prosthesis 13.

Referring now to FIGS. 7 and 7A, a finned glenoid prosthesis 17 is shown. The finned prosthesis 17 includes grooves 19 located on fin 18 of the prosthesis 17. The prosthesis 17 is also used with cement 20. As can be seen, the finned prosthesis 17 also requires a subcondylar plate to properly support the prosthesis 17.

Referring now to FIG. 8, an anchor peg prior art glenoid prosthesis 21 is shown. The anchor peg prosthesis 21 includes cement pegs 22 as well as anchor peg 24. The anchor peg 24 may be press fitted for bone ingrowth while the cement pegs 22 are secured to the glenoid articulating surface with cement 23. The anchor peg glenoid 21 also depends on the quality of the subcondylar plate.

Referring now to FIG. 9, yet another prior art glenoid prosthesis is shown as a metal backed glenoid with a screw 25. The glenoid prosthesis 25 includes a metal backing 26 that supports a screw 27 that is fitted into scapula 28. The metal backed with screw glenoid prosthesis 25, as shown in FIG. 9, also requires a well preserved subcondylar plate to properly support the prosthesis 25.

As can be shown in FIGS. 1 through 9, in many cases the subcondylar plate defects and the underlying cancellous bone defects increase the difficulty in achieving appropriate prosthesis fixation and support. A need, therefore, exists for a glenoid prosthesis for use in a patient with a damaged or missing subcondylar plate.

SUMMARY

The present invention provides for a glenoid component and system that has fixation to the inside walls of the glenoid vault and provides compressive load support from the remaining glenoid cortical rim. The present invention provides for a glenoid resurfacing prosthesis with particular application for treatment of posterior erosion and revision applications. For the resurfacing prosthesis of the present invention, the fixation and stabilization of the prosthetic component occurs inside the glenoid vault.

According to the present invention, a glenoid component system may be provided with multiple variable size variations to accommodate variations in the human anatomy. Glenoid components consist of both concave lateral surfaces for articulation with a prosthetic humeral head and medial body configured for fixation against the inner wall of the glenoid vault. The rim of the concave articulating surface is configured to rest against the remaining glenoid cortical rim.

The medial body configuration can be of a all polyethylene design for fixation against the inner wall of the glenoid vault with bone cement. It can also be designed with a metal porous coating backing and holes to accept bone screws. The bone screws are used to provide initial fixation until bone ingrowth occurs on the porous surfaces of the metal backing member. Also the prosthesis can be configured to replace lost bone when posterior erosion of the glenoid surface has occurred.

According to one embodiment of the present invention, there is provided a glenoid component for use with a prosthetic humeral component for use in performing shoulder arthroplasty. The glenoid component may be fitted at least partially into a cavity formed in the glenoid vault. The glenoid component includes a body having a stem portion for inserting at least partially into the cavity formed in the glenoid vault. The stem portion cooperates with the interior wall of the cavity formed in the glenoid vault. The body has a bearing portion for articulating cooperation with the prosthetic humeral component.

According to another embodiment of the present invention there is provided a tamp for use in forming grafting material into a cavity in the glenoid vault to prepare the vault for a glenoid component for performing shoulder arthroplasty. The tamp includes a body and a forming portion extending in a first direction from the body. The forming portion has a surface shaped to receive the glenoid component.

According to a further embodiment of the present invention, there is provided a method for providing shoulder arthroplasty. The method includes the steps of resecting a glenoid vault, providing a tool for forming a cavity in the glenoid vault, forming a cavity in the glenoid vault with the tool, providing a glenoid prosthetic component for at least partially fitting into the cavity in the glenoid vault, and implanting the glenoid prosthetic component in the cavity.

According to yet another embodiment of the present invention there is provided a kit for use in performing shoulder arthroplasty. The kit includes a tool for use in forming a cavity in the glenoid vault for performing shoulder arthroplasty. The kit also includes a glenoid component for use with a prosthetic humeral component.

The technical advantages of the present invention include the ability to provide a glenoid prosthesis that does not depend upon the condition of the patient's subcondylar plate. For example, according to one aspect of the present invention, a glenoid prosthesis is provided which substantially fills the glenoid vault and provides complete support under the articulating surface of the glenoid prosthesis. Thus, the present invention provides for improved support of the glenoid prosthesis independent of the condition of the subcondylar plate.

Another technical advantage of the present invention includes the ability to provide for an effective glenoid prosthesis when the cortical walls of the glenoid vault are severely damaged. For example, according to one aspect of the present invention, the prosthesis includes metal walls that substitute for a portion of the cortical walls of the glenoid vault.

Yet another technical advantage of the present invention includes the ability to provide for a glenoid prosthesis when the cancellous bone in the glenoid vault has voids. For example, according to one aspect of the present invention, the glenoid vault is cleaned and removed of cancellous bone. The glenoid vault then is filled with a combination of bone graft and/or cement, and the prosthesis of the present invention that fills a substantial portion of the glenoid vault is implanted. Thus, the present invention provides for a glenoid prosthesis that is suitable to be used where the glenoid vault includes voids of cancellous bone.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which:

FIG. 6 is a top view partially in cross section of a prior art cemented pegged glenoid component in position on a human glenoid for use with a prosthetic humeral component for use in performing shoulder joint arthroplasty;

FIG. 7 is a top view partially in cross section of a prior art cemented finned glenoid component in position on a human glenoid for use with a prosthetic humeral component for use in performing shoulder joint arthroplasty;

FIG. 7A is a medial/lateral view partially in cross section of the FIG. 7 finned glenoid component in position on a human glenoid;

FIG. 8 is a top view partially in cross section of a prior art non-cemented anchor peg glenoid component in position on a human glenoid for use with a prosthetic humeral component for use in performing shoulder joint arthroplasty;

FIG. 9 is a top view partially in cross section of a prior art non-cemented metal backed glenoid component with screw in position on a human glenoid for use with a prosthetic humeral component for use in performing shoulder joint arthroplasty;

FIG. 16 is a plan view of a tamp for use with the vault fixed (biological and/or cemented) glenoid component of FIGS. 13 and 14;

FIG. 17 is an end view of the tamp of FIG. 16;

FIG. 28 is a top view of a template for preparing a resected surface for the implantation of a metal backed glenoid;

FIG. 29 is a plan view partially in cross section of the template of FIG. 28; and FIG. 30 is a tool for use with the template of FIG. 28.

DETAILED DESCRIPTION

Embodiments of the present invention and the advantages thereof are best understood by referring to the following descriptions and drawings, wherein like numerals are used for like and corresponding parts of the drawings.

Figure 1:
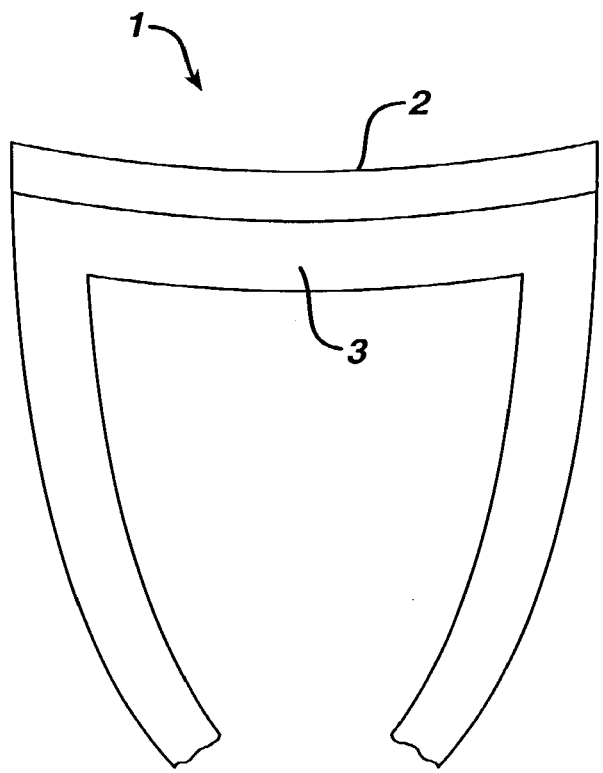
FIG. 1 is a top view partially in cross section of a healthy human glenoid.
Figure 2:
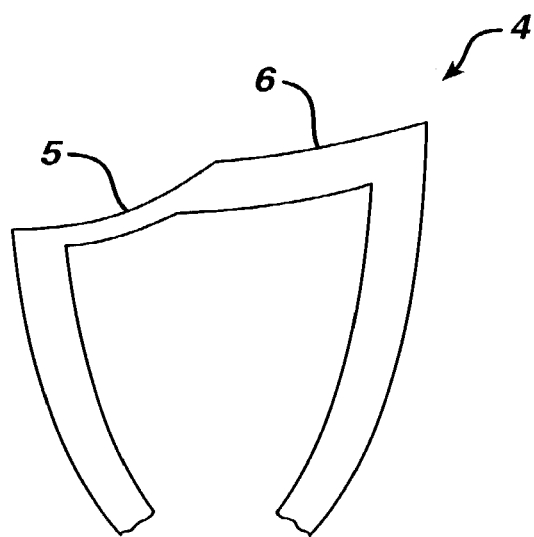
FIG. 2 is a top view partially in cross section of a human glenoid with posterior erosion.
Figure 3:
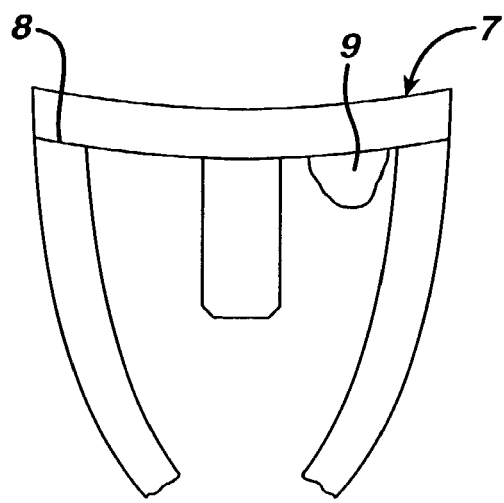
FIG. 3 is a top view partially in cross section of a failed human glenoid.
Figure 4:
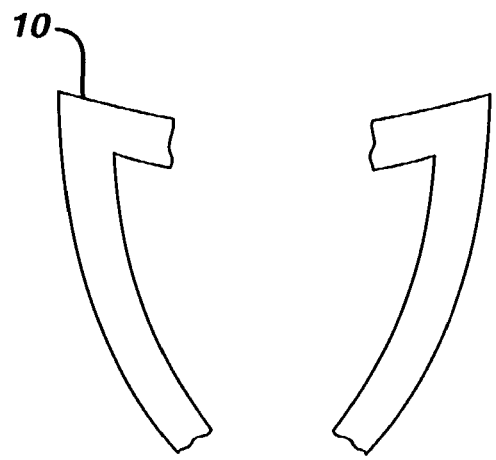
FIG. 4 is a top view partially in cross section of a prior art glenoid component in position on an eroded human glenoid for use with a prosthetic humeral component for use in performing shoulder joint arthroplasty.
Figure 5:
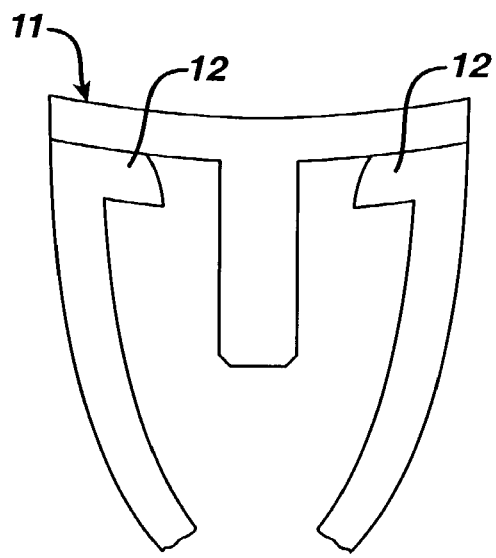
FIG. 5 is a top view partially in cross section of a prior art glenoid component in position on a failed human glenoid for use with a prosthetic humeral component for use in performing shoulder joint arthroplasty.
Figure 10:
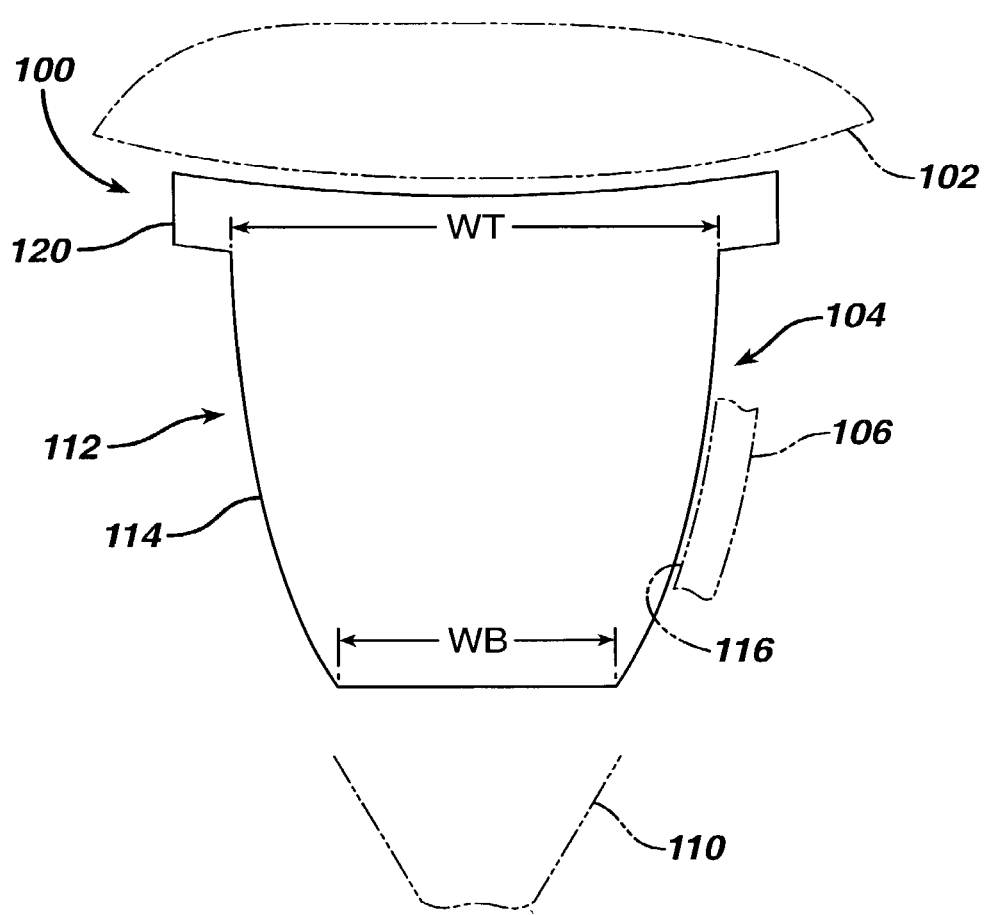
FIG. 10 is a top view partially in cross section of a one-piece vault fixed glenoid component for use with a prosthetic humeral component for use in performing shoulder joint arthroplasty, the glenoid component closely conforming to the glenoid vault, in accordance with an embodiment of the present invention.
Figure 11:
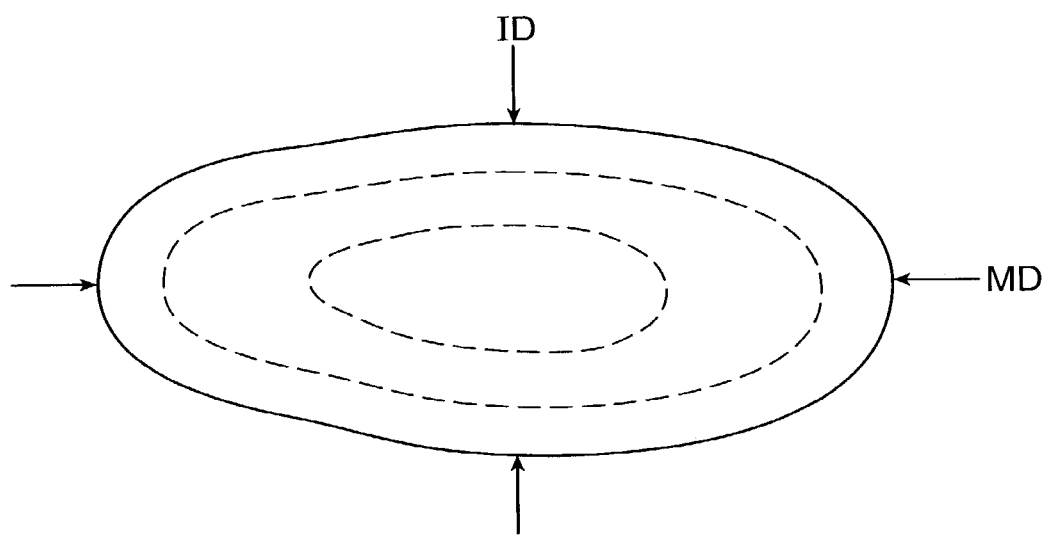
FIG. 11 is an end view of the glenoid component of FIG. 10.

According to the present invention referring now to FIGS. 10 and 11, a glenoid component 100 for use with a prosthesis humeral component 102 for use in shoulder arthroplasty is shown. The glenoid component 100 is fitted at least partially into a cavity 104 formed in the glenoid vault 106 of the scapula 110. The glenoid component 100 includes a body 112 having a stem portion 114 for inserting at least partially into the cavity 104 formed in the glenoid vault 106. The stem portion 114 cooperates with the interior wall 116 of the cavity 104 formed in the glenoid vault 106. The body 112 also includes a bearing portion 120 for articulating cooperation with the prosthetic humeral component 102.

The glenoid component 100 may be made of any suitable durable material. For example, the glenoid component 100 may be made of a plastic. For example, the glenoid component 100 may be made of a polyethylene. One particular polyethylene that is well suited for a bearing portion is a high molecular weight polyethylene, for example ultra-high molecular weight polyethylene (UHMWPE). One such UHMWPE is sold by the assignee of the instant application or Marathon™ UHMWPE and more fully described in U.S. Pat. Nos. 6,228,900 and 6,281,264 to McKellop incorporated herein in their entireties by reference.

The glenoid component 100 may have any suitable shape capable of filling a substantial portion of the cavity 104. The glenoid cavity 104 may vary substantially from patient to patient. Generally, however, the cavity 104 has a generally inverted dome shape and has a generally oval cross-section. Preferable the glenoid component 104 likewise has a oval domed shape to correspondence to that of the cavity 104. For example, referring to FIG. 10, the stem portion 114 of the glenoid component 100 has a generally domed shape with a larger width WT adjacent the bearing portion 112 and a small diameter WB at the stem portion 112 opposed to the bearing portion 120.

Referring to FIG. 11, the glenoid component 100 is preferably generally oval with a major diameter MD that is substantially larger than the minor diameter ID. While the glenoid component 110 preferably has a shape similar to that of the cavity 104, it should be appreciated that the glenoid component 100 may completely fill the cavity 104 or the somewhat smaller than the cavity 104.

As shown in FIGS. 10 and 11, the glenoid component 100 is in intimate contact with the glenoid vault 106 to assist in the secure location of the glenoid component 100. Exact sizing of the glenoid component 100 to the cavity 104 maybe somewhat difficult due to the unique anatomy of every individual. It should be appreciated that a series of glenoid components 100 may be provided for accommodating the most common sizes of the glenoid cavity for various patients.

Figure 12:
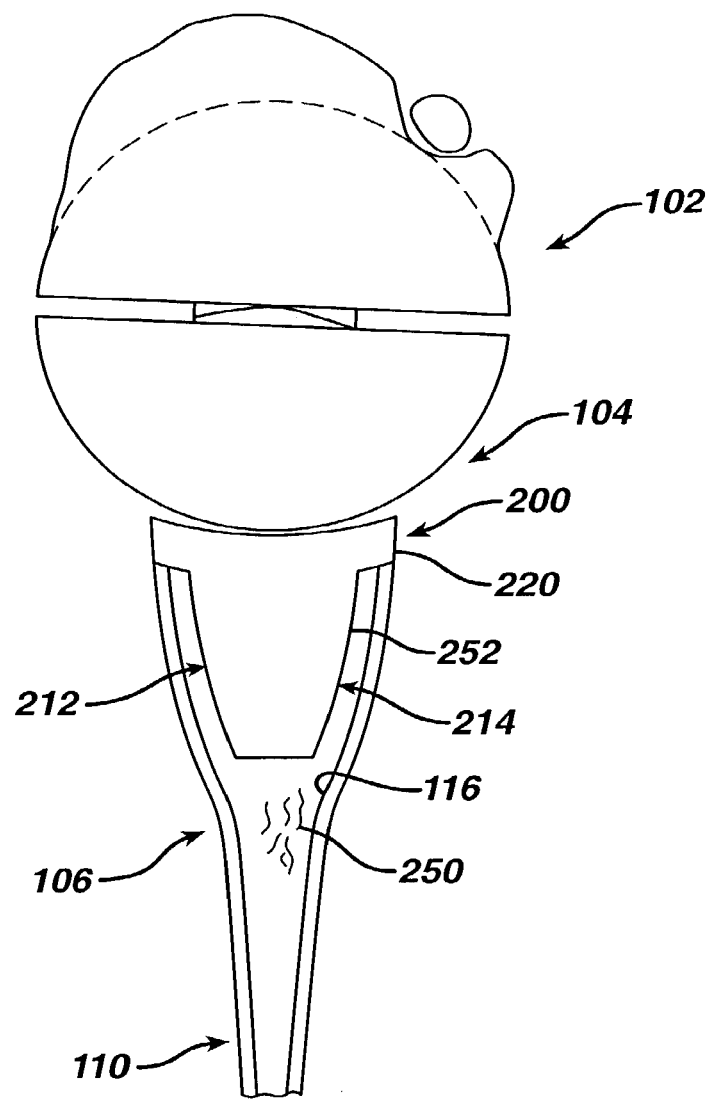
FIG. 12 is a top view of another embodiment of the present invention in the form of a shoulder prosthesis assembly using the a one-piece vault fixed glenoid similar to that of FIG. 10.

Referring now to FIG. 12, an alternative embodiment of the present invention is shown as glenoid component 200 for use with humeral component 102. The glenoid component 200 of FIG. 12 is similar to the glenoid component 100 of FIGS. 10 and 11, except that the glenoid component 200 includes a stem portion 214 which is sized relatively smaller than the stem portion 114 of the glenoid component 110 of FIGS. 10 and 11 so that cement 250 may be positioned between internal wall 116 of the glenoid vault 106 and stem periphery 252 of the stem portion 214 of the glenoid component 200. The cement 250 may be any suitable cement capable of assisting and securing the glenoid component 200 to the glenoid vault 106. For example the cement may be polymethylmenthacrylate (PMMA).

The glenoid component 200 may as shown in FIG. 12 be an integral component such as glenoid component 100 and may, for example be made of a plastic for example high molecular weight polyethylene or ultra high molecular weight polyethylene. The glenoid component 200 includes a body 212 having a stem portion 214 and a bearing portion 220. The use of the cement 250 permits the use of a common glenoid component 200 for varying sizes of the glenoid vault.

Figure 13:
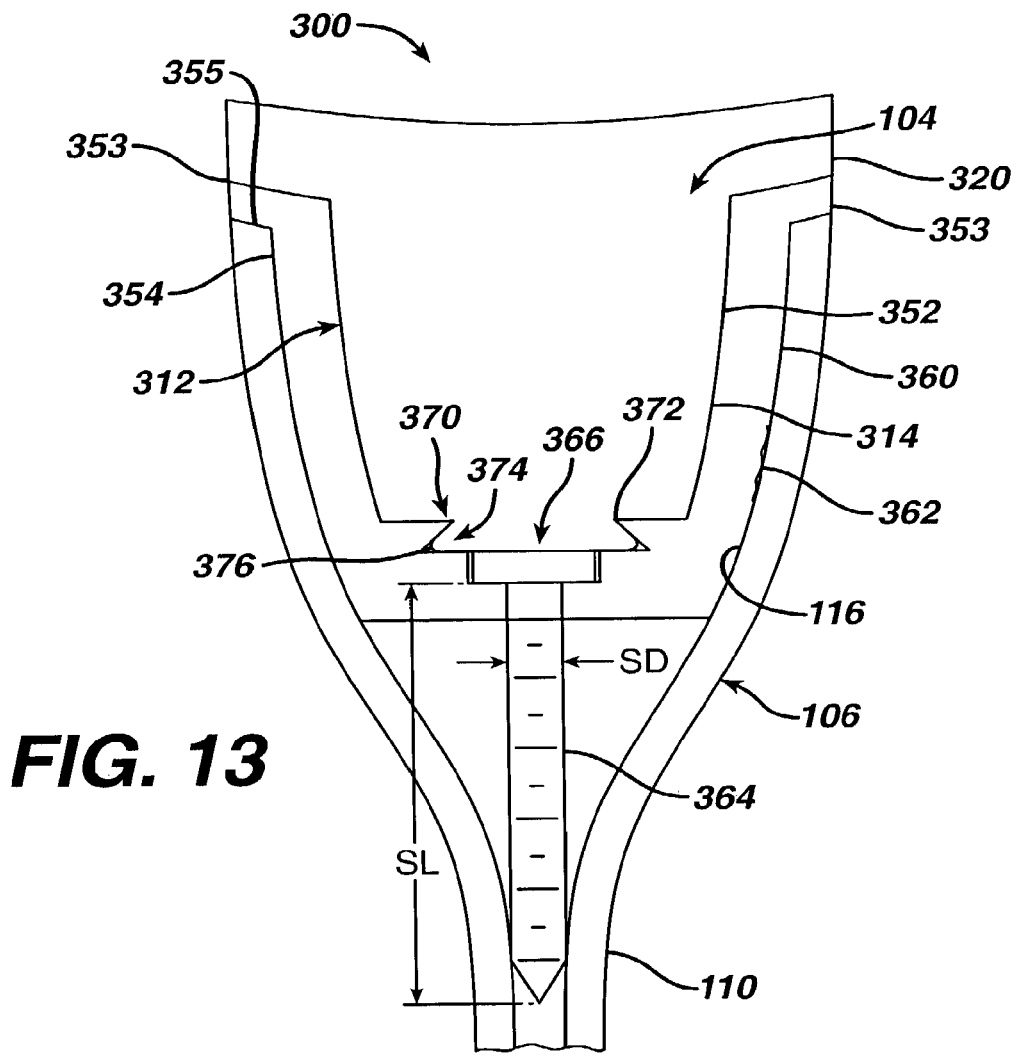
FIG. 13 is a top view partially in cross section of a vault fixed (biological and/or cemented) glenoid component with optional screw for use with a prosthetic humeral component for use in performing shoulder joint arthroplasty, in accordance with another embodiment of the present invention.
Figure 13A:
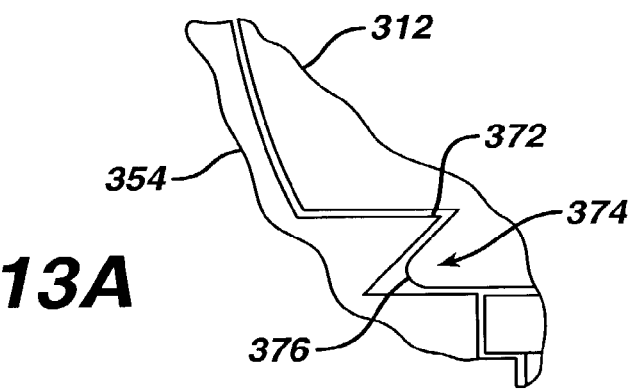
FIG. 13A is a partial top view partially in cross section of the vault fixed glenoid component of FIG. 13.
Figure 14:
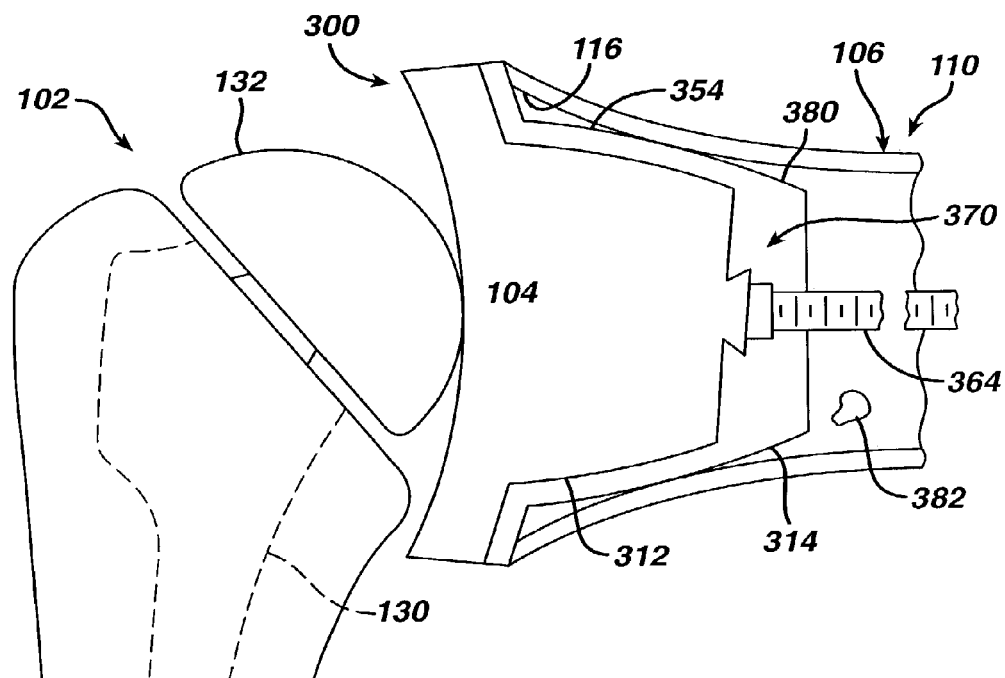
FIG. 14 is a medial/lateral view of the shoulder prosthesis assembly using the metal backed glenoid of FIG. 13.

Referring now to FIGS. 13, 13A, and 14, another embodiment of the present invention is shown as glenoid component 300. Glenoid component 300 is similar to the glenoid component 200 except that the glenoid 300 further includes a support layer 354 surrounding a portion of body 312 of the glenoid component 300.

The glenoid component 300 includes a body 312 having a stem portion 314 and a bearing portion 320. The support layer 354 extends outwardly from stem periphery 352 of the stem portion 314 of the body 312 of the glenoid component 300. As shown in FIG. 13, the support layer 354 may include a lip 353 which extend outwardly from the distal end of the support layer 354. The lip 353 rests on cortical wall 355 and provides support for the glenoid component 300. The support layer 354 may be made of any suitable durable material and may be made as a metal compatible with the human anatomy, for example, a cobalt chromium alloy, a stainless steel alloy or a titanium alloy.

Support layer periphery 360 of the support layer 354 may, as shown in FIG. 13, be in intimate contact with inner wall 116 of the glenoid vault 106. The support layer periphery 360 may include a porous coating 362 to assist in the bone in growth of the glenoid component 300 to the glenoid vault 106.

The coating 362 may be any suitable porous coating and may for example be Porocoat®, a product of the assignee of the instant application and more fully described in U.S. Pat. No. 3,855,638 to Pilliar hereby incorporated by reference in its entireties.

As shown in FIG. 13, the glenoid component 300 may further include a fastener 364 in the form of, for example, a screw.

The screw 364 may be any screw capable of assisting and securing the glenoid component 300 to the glenoid vault 106. For example, the screw 364 may be in the form of a cortical screw, for example, a cortical screw available from DePuy Orthopaedics, Inc. the Assignee of the instant application. One such cortical screw is DePuy Ace catalog number 8150-36-030.

The screw 364 has a diameter SD of sufficient diameter to properly secure the glenoid component 300 to the glenoid vault 106 and may, for example, have a diameter SD of about two to five millimeters. The screw 364 may have any suitable length capable of properly securing the glenoid component 300 to the glenoid vault 106 and reaching sufficient bone in the scapula 110 to properly secure the glenoid component 300. For example, the screw 364 may have a length of SL of from 10 to 60 millimeters.

The screw 364 may be secured to the glenoid component 300 in any suitable fashion and may, as shown in FIG. 13, be secured to the support layer 354 of the glenoid component 300. The support layer 354 may include an opening 366 through which the screw 364 partially passes.

The support layer 354 may be secured to the body 312 in any suitable manner For example, the support layer 354 may be bonded to the body 312. For example, the support layer 354 could be made of polyethylene and compression molded to the body 312. Alternately the support layer 354 may be glued to the body 312 by, for example, an adhesive.

Alternatively the support layer 354 may be mechanically interlocked to the body 312. For example, the support layer 354 may include surface features, for example, ribs (not shown) or perhaps a porous coating to mechanically interlock the support layer 354 to the body 312.

Alternatively and as shown in FIGS. 13 and 13A, the glenoid component 300 may include a locking feature 370. The locking feature 370 may have any shape capable of mechanically locking the support layer 354 to the body 312. For example, the support layer 354 may include a lip 372 that forms a groove 374 in the support layer 354. The body 312 may include a protrusion 376 that matingly fits with the groove 374 to secure the body 312 and the support layer 354 to each other. It should be appreciated that the protrusion 376 may be in the form of separate spaced-apart detents or may be in the form of a circular ring.

When installing the glenoid component 300, the support layer 354 is first placed in the glenoid vault 106 and the screw 364 is positioned through the opening 366 and engages the scapula 110. After the screw 364 is fully inserted, the body 312 may be placed into the support layer 354 with the protrusion 376 being snapped into the groove 374 of the support layer 354.

As shown in FIG. 13 when viewing the glenoid vault 106 from above, the support layer 354 may closely conform to the glenoid vault 106. Further, when viewing the glenoid component 300 and the glenoid vault 106 in the medial lateral view of FIG. 14, the glenoid vault 106 curves inwardly in the proximal direction with a shape that could be described as that of a wine glass.

During the revision shoulder arthroplasty surgery, the cancellous bone within the cavity 104 is generally removed and the glenoid cavity 104 is cleaned to the inner wall 116 of the glenoid vault 106. It is thus desirable to support the glenoid component 300 between the support layer 354 and the inner wall 116 of the glenoid vault 106. A material suitable for supporting the glenoid component 300 is preferably positioned in the glenoid vault 106. Such a material is graft mineralized bone fragments that are commercially available or created from the patient's available bone.

Continuing to refer to FIG. 14, the cavity 104 between inner wall 116 of glenoid vault 106 and body support layer surface 380 of the support layer 354 of the glenoid component 300 is preferably filled with a mineralized bone graft material 382.

Figure 15:
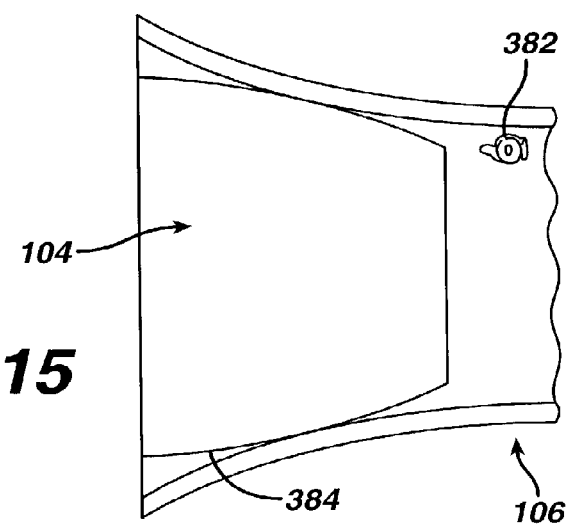
FIG. 15 is a medial/lateral view of a glenoid vault showing mineralized bone having been positioned in the glenoid cavity with the TAMP of FIGS. 16 and 17.

Referring now to FIG. 15, the glenoid vault 106 is shown with the mineralized bone graft material 382 in position in the cavity 104. The mineralized bone graft material 382 is preferably positioned with an outer contour 384 that conforms to the body support layer surface 380 of the glenoid component 300.

Referring now to FIGS. 16 and 17, another embodiment of the present invention is shown as tamp 386. The tamp 386 is for use in forming the grafting material 382 (see FIG. 15) into the cavity 104 of the glenoid vault 106 to prepare the vault 106 for the glenoid component 300 for performing shoulder arthroplasty.

The tamp 386 includes a body 390. The body 390 may have any suitable shape and may as is shown in FIGS. 16 and 17 have a generally cylindrical elongated shape. The tamp 386 further includes a forming portion 392 extending in a first direction from the body 390. The forming portion 392 includes a surface 394 of the forming portion 392 that is shaped to receive the glenoid component 300 (see FIGS. 13 and 14). Preferably, the outer surface 394 of the forming portion 392 has a shape that is substantially similar to that of the outer surface 380 of the glenoid component 300 (see FIG. 14).

As shown in FIGS. 16 and 17, the tamp 386 may further include a handle 396 which may be located opposed to the forming portion 392. The handle 396 may serve to provide a place to hold the tamp 386 when it is being used to position and tamp the graft material 382. Further, the handle 396 may include a surface 398 for striking the tamp 386 to properly secure the graft material 382. The tamp 386 may further include a stop 399 positioned between the body 390 and the forming portion 392. The stop 399 may be used to limit the motion of the tamp 386 and to provide for an accurate shape of the graft material 382 by resting the stop 399 against the glenoid vault 106.

While the forming portion 392 may have any suitable shape, the forming portion 392 preferably conforms to the shape of the glenoid component 300. While the glenoid component 300 may be circular, preferably to conform to the shape of the glenoid vault 106, the glenoid component 300 is generally oval. Therefore, as shown in FIGS. 16 and 17, the forming portion 392 has an outer periphery 394 that is generally oval.

The tamp 386 may be made of any suitable durable material and may, for example, be made of a titanium alloy, a cobalt chromium metal alloy, or a stainless steel alloy. The tamp 386 may be integral or may be made of various components which are mechanically interlocked to each other.

Figure 18:
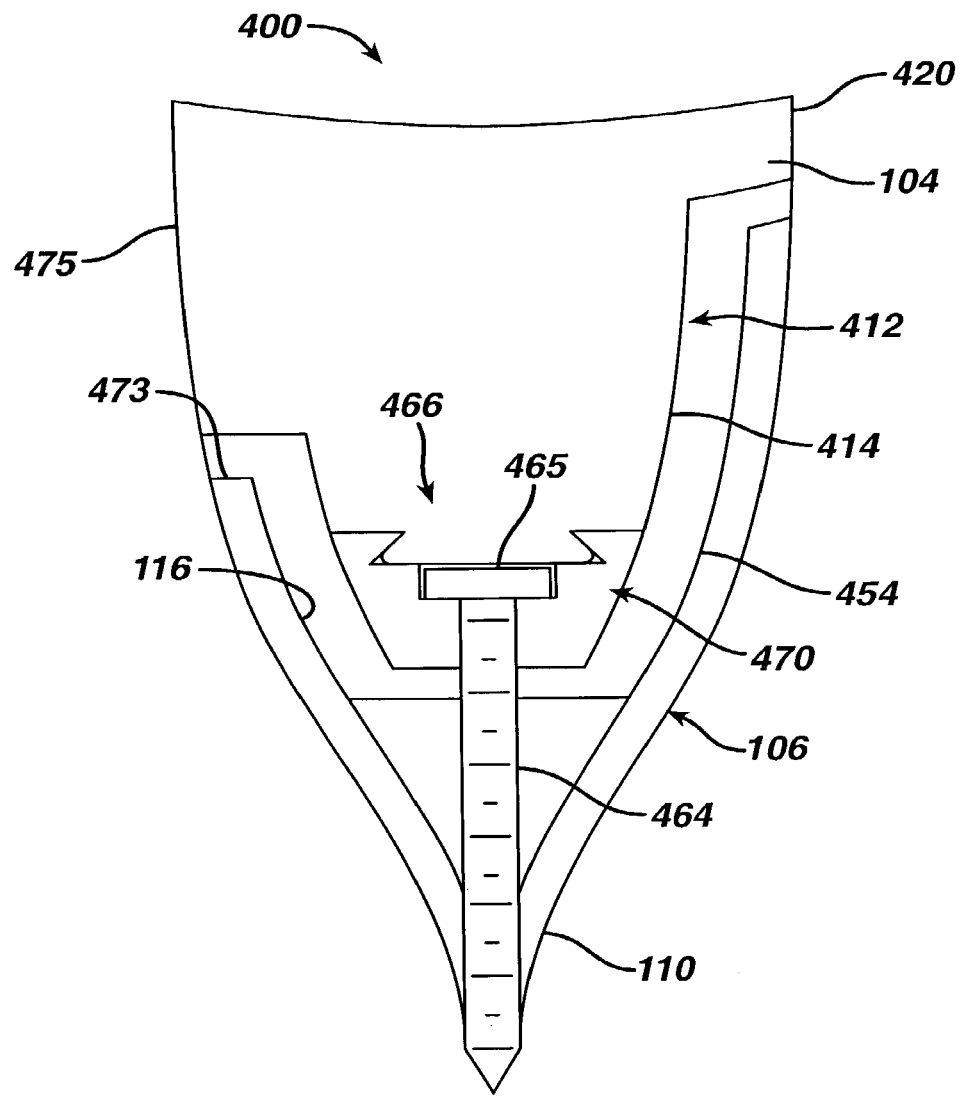
FIG. 18 a top view partially in cross section of a metal backed vault fixed (biological and/or cemented) glenoid component with screw for use with a prosthetic humeral component for use in performing shoulder joint arthroplasty where there is posterior erosion, in accordance with a further embodiment of the present invention.
Figure 19:
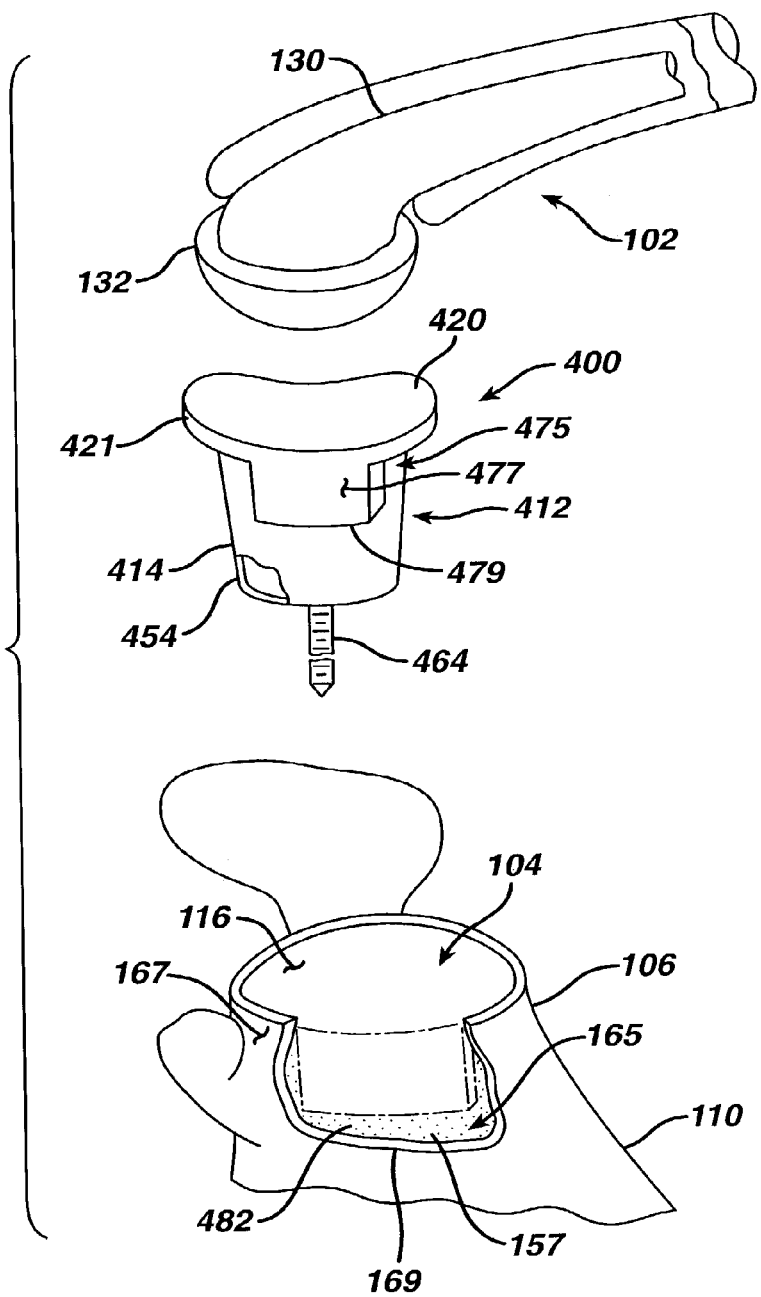
FIG. 19 is an exploded perspective view of a shoulder prosthesis assembly in position in a humerus and a glenoid cavity using the FIG. 18 metal backed vault fixed glenoid component with screw for use in performing shoulder joint arthroplasty where there is posterior erosion.

Referring now to FIGS. 18 and 19, another embodiment of the present invention is shown as glenoid component 400. Glenoid component 400 is similar to glenoid component 300 of FIGS. 13 and 14 except that glenoid component 400 is designed to accommodate those patients in whom at least a portion of the glenoid vault 106 is damaged or missing.

Referring now to FIG. 19, the glenoid vault 106 of the scapula 110 is shown having a void 165 in the vault periphery 167 of the glenoid vault 106. A purpose of the glenoid component 400 is to replace at least a portion of the void 165 in the vault periphery 167. The glenoid component 400 thus includes a vault replacement portion 475.

The vault replacement portion 475 extends downwardly from bearing portion 420 of the glenoid component 400. The vault replacement portion 475 extends from bearing portion periphery 421 of the bearing portion 420 of the glenoid component 400. The outer surface 477 of the vault replacement portion 475 extends from the bearing portion periphery 421 and is aligned with vault periphery 167 of the glenoid vault 106.

In order to provide a glenoid component 400 that is commercially available, the glenoid component 400 includes a vault replacement portion 475 that has a vault replacement portion edge periphery 479 that is smaller and extends within edge periphery 169 of the void 165 in the glenoid vault 165. The glenoid component 400 includes the bearing portion 420 that is similar to the bearing portion 320 of the glenoid component 300 of FIGS. 13 and 14. The bearing portion 420 mates with the humeral head 132 of the humeral component 102.

The glenoid component 400 also includes a body 412 that is similar body 312 of the glenoid component 300 of FIGS. 13 and 14. The body 412 also includes a stem portion 414 that is similar to stem portion 314 of the bearing component 300 of FIGS. 13 and 14, except that the stem portion 414 further includes the vault replacement portion 475.

To accommodate the space between the void 165 in the glenoid vault 106 and the vault replacement portion 475, the gap 157 between the vault replacement portion 475 and the glenoid vault 106 may be filled with, for example, graft material 482 similar to the graft material 382 of the glenoid component 300 of FIGS. 13 and 14.

Referring again to FIG. 18, the glenoid component 400 includes, in addition to the body 412, a support surface 454 similar to the support layer 354 of the glenoid component 300 of FIGS. 13 and 14, except that the support layer 454 does not extend into the vault replacement portion 475 of the body 412.

The glenoid component 400 may further include a screw 464 similar to the screw 364 of the glenoid component 300 of FIGS. 13 and 14. The screw 464 may be secured to the support layer 454 by means of, for example, a screw head 465 which mates with the support layer 454 of the glenoid component 400. The screw 464 passes through opening 466 in the support layer 454. The screw 464 is similar to the screw 364 of the glenoid component 300 of FIGS. 13 and 14.

The body 412 may be made of any suitable material and may for example be made of materials similar to that of the body 312 of the glenoid component 300 of FIGS. 13 and 14. The body 412 may be secured to the support layer 454 in any suitable method and may, for example, be secured in a method similar to that of the glenoid component 300 and may, for example, include a locking feature 470 similar to the locking feature 370 of the glenoid component 300.

While the vault replacement portion 475 of the glenoid component 400 of FIGS. 18 and 19 may be a portion of the body 412 and be made of, for example, a plastic, it should be appreciated that the vault replacement portion 475 may be a part of the support layer 454.

Figure 20:
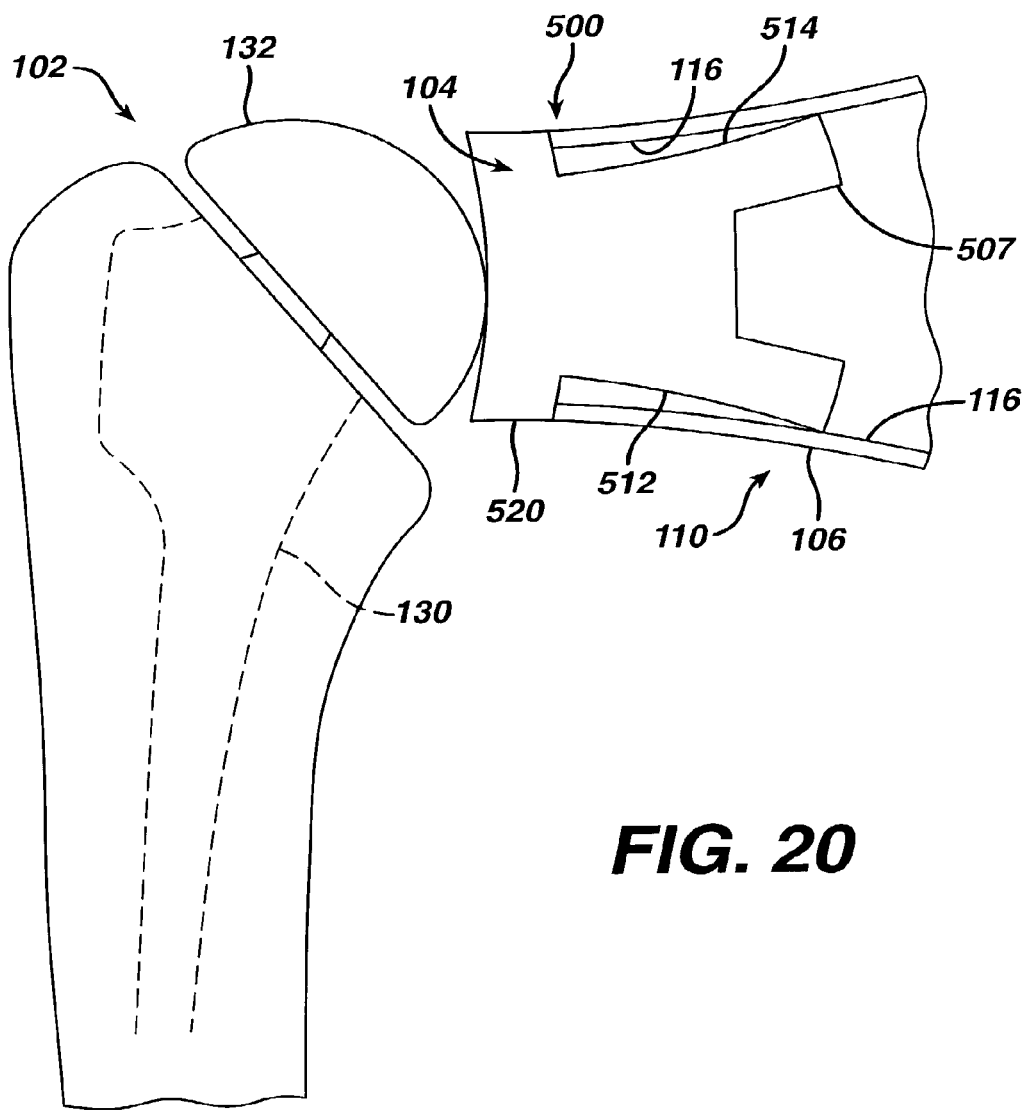
FIG. 20 is a medial/lateral view of a shoulder prosthesis assembly using a resilient one-piece glenoid for cementless application in accordance with yet another embodiment of the present invention.
Figure 21:
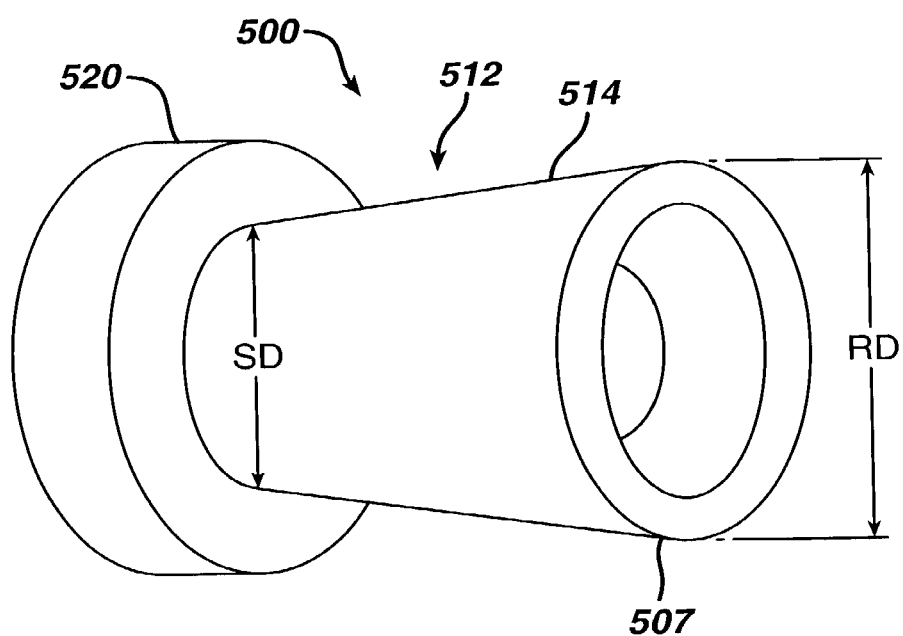
FIG. 21 is a partial perspective view of the glenoid component of FIG. 20.
Figure 22:
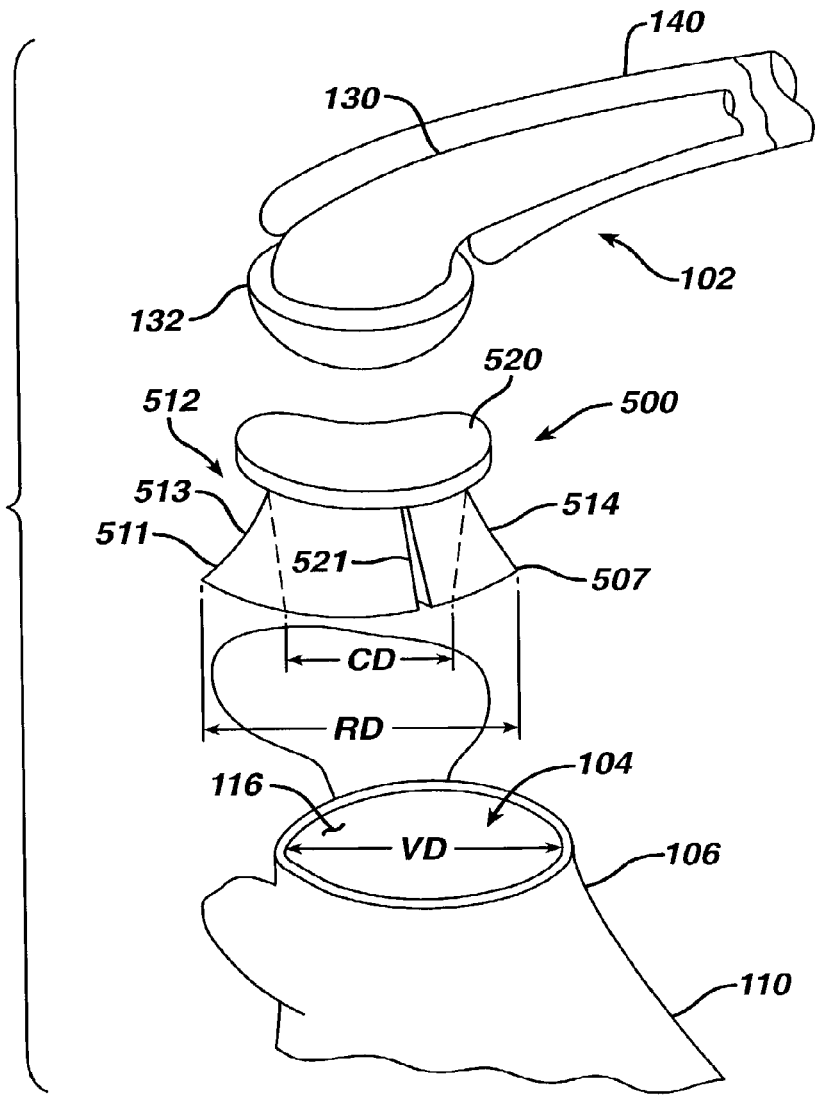
FIG. 22 is an exploded perspective view of the shoulder prosthesis assembly of FIG. 19.

Referring now to FIGS. 20, 21 and 22, another embodiment of the present invention is shown as glenoid component 500. Glenoid component 500 is similar to glenoid component 100 of FIGS. 10 and 11 except that glenoid component 500 includes a resilient integral portion 507 which is conformable to be positionable within the glenoid vault 106 and expands on being positioned in the glenoid vault 106 to conform to the inner walls 116 of the glenoid vault 106.

As shown in FIG. 20, the glenoid component 500 includes a body 512, which body 512 includes a stem portion 514 and a bearing portion 520. The bearing portion 520 is similar to the bearing portion 120 of the glenoid component 100 of FIGS. 10 and 11. The stem portion 514 includes a resilient integral portion 507 that expands to conform to the inner walls 116 of the glenoid vault 106. The resilient integral portion 507 may, as shown in FIG. 20, be in the form of a lip 507.

Referring now to FIG. 22, the glenoid component 500 is shown positioned between the prosthetic humeral component 102 and the glenoid vault 106. The bearing portion 520 of the glenoid component 500 mates with head 132 of the prosthetic humeral component 102. The lip 507 of the glenoid component 500 is shown in solid in a relaxed position 511 and in phantom in a constrained position 513.

When in the constrained position 513, the lip 507 has a constrained diameter CD that is equal to or smaller than the vault diameter VD of the glenoid vault 106. Therefore, the stem portion 514 of the glenoid component 500 can be positioned in the glenoid cavity 104 of the scapular 110. Upon insertion into the glenoid cavity 104, the lip 507 returns to the relaxed diameter RD that is larger than the vault diameter VD of the glenoid cavity 104. Thus, the glenoid component 500 is constrained within the glenoid vault 106.

The glenoid component 500 may be made of any suitable durable material and may, as shown in FIGS. 21 and 22 be integrally molded of a plastic. For example, the glenoid component 500 may be made of a polyethylene, for example ultra-high molecular weight polyethylene. It should be appreciated that the stem portion 514 may include one or more slit 521 to permit the stem portion 514 to have greater flexibility to permit the expansion and contraction of the lip 507 to fit within the glenoid vault 106.

Referring now to FIG. 21, the lip 507 is shown in greater detail. The lip 507 has a relaxed diameter RD that is larger than the stem diameter SD of the stem 514 of the glenoid component 500.

Figure 23:
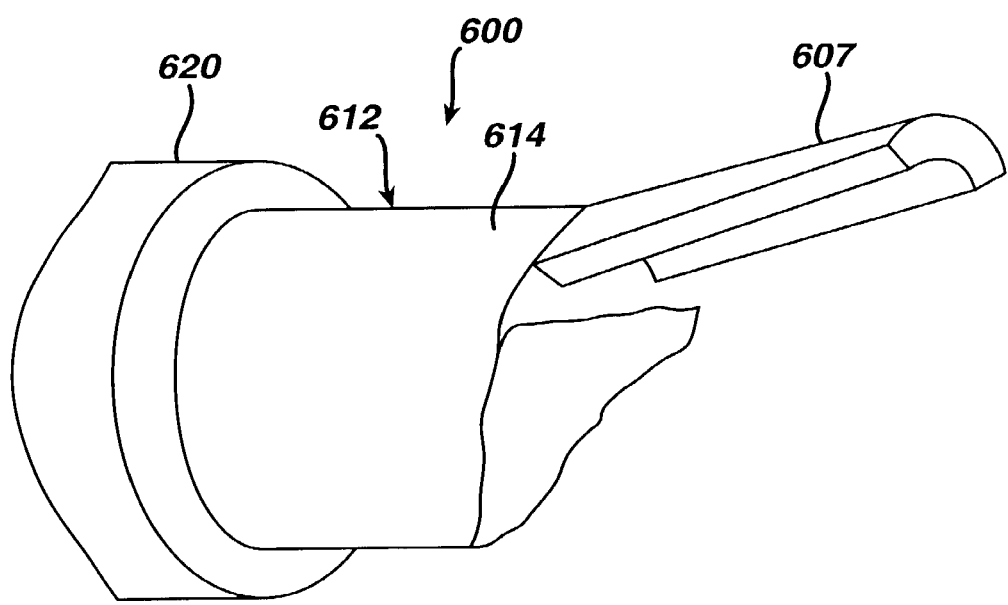
FIG. 23 is a partial perspective view of the glenoid component with resilient glenoid vault contacting fingers in accordance with yet another embodiment of the present invention.

Referring now to FIG. 23, an alternate embodiment of the present invention is shown as glenoid component 600. Glenoid component 600 is similar to glenoid component 500 of FIGS. 20, 21 and 22, except that glenoid component 600 includes a plurality of fingers 607 which serve the purpose of the lip 507 of the glenoid component 500. The glenoid component 600 thus includes a body 614 which includes a bearing portion 620 similar to the bearing portion 520 of the glenoid component 500 of FIGS. 20, 21 and 22, as well as a stem portion 614 which is different than the stem portion 514 of the glenoid component 500 of FIGS. 20, 21 and 22 in that the stem portion 614 includes the fingers 607.

Figure 24:
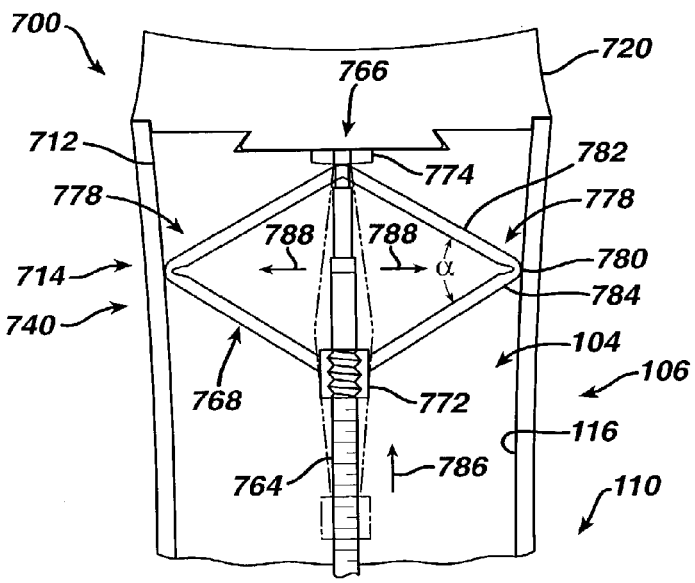
FIG. 24 is a plan view partially in cross section of a umbrella type mechanically expandable vault fixed (cementless) glenoid component for use with a prosthetic humeral component for use in performing shoulder joint arthroplasty in accordance with yet another embodiment of the present invention.

Under the present invention and referring now to FIG. 24, another embodiment of the present invention is shown as glenoid component 700. The glenoid component 700 is similar to the glenoid component 300 of FIGS. 13 and 14 except that the stem component 714 is in the form of an expander 740. The glenoid component 700 includes a body 712, which includes a stem portion 714 and a bearing portion 720.

The bearing portion 720 may be integral with the body 712 or, as shown in FIG. 24, the bearing component 720 may be a separate component. If the body 712 and the bearing component 720 are made of a integral component, the body 712 is preferably made of a plastic, for example ultra-high molecular weight polyethylene. It should be appreciated, however, that the body 712 may likewise be made of a durable metal compatible with the human body.

If the body 712 and the bearing component 720 are made of separable components as shown in FIG. 24, the body 712 is preferably made of a metal. For example, the body 712 may be made of a cobalt chromium alloy, a titanium alloy, or a stainless steel alloy. The bearing component 720, if made of a separable component, is preferably made of a plastic, for example an ultra-high molecular weight polyethylene.

A locking feature 770 that is similar to the locking feature 370 of the glenoid component 300 of FIGS. 13 and 14 may be used for securing the bearing portion 720 to the body 712. The expander 470 is operably connected to the body 712 through, for example, a opening 766 in the body 712.

The expander 740 is positioned at least partially within the cavity 104 of the glenoid vault 106. A portion of the expander 740 may be urged against inner walls 116 of the glenoid vault 106. The expander 740 may, as shown in FIG. 24, include a screw 764 that is fitted through opening 766 in the body 712. The screw 764 may be any commercially available bone screw similar to bone screw 364 of the glenoid component 300 of FIGS. 13 and 14. The screw 764 engages cortical bone in the scapula 110.

Figure 24A:
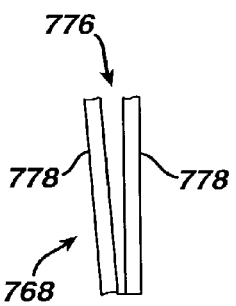
FIG. 24A is a partial plan view of the expander of FIG. 24.

The screw 764 is threadably secured to a tube 768 at threaded end 772 of the tube 768. The tube 768 is in clearance with the screw 764 on bearing end 774 of the tube 768. Longitudinal slits 776 are formed in the tube 768 and form staves 778 between the threaded end 772 and the bearing end 774 see (FIG. 24A).

Referring again to FIG. 24, the staves 778 have crimped portions 780 equidistant from the bearing end 774 and the threaded end 772. The crimped portions 780 separate upper stave portions 782 from lower stave portions 784. As the threaded end 772 is moved upwardly in the direction of arrow 786, the staves 778 are bent with the upper stave portion 782 and the lower stave portions 784 forming an angle .alpha. there between.

When the glenoid component 700 is positioned in vault 106, the screw 764 is rotated causing the screw 764 to engage the scapula 110 and causing the threaded end 772 of the tube 768 to move in the direction of arrow 786 causing the crimped sections 780 of the staves 778 to move in the direction of arrows 788 toward inner walls 116 of the glenoid vault 106, thereby securing the glenoid component 700 to the glenoid vault 106.

The tube 768 may be made of any suitable durable material and may, for example, be made of a flexible metal compatible with the human body, for example a titanium alloy. It should be appreciated that the tube 768 may be made of a stainless steel alloy or a cobalt chromium alloy.

Figure 25:
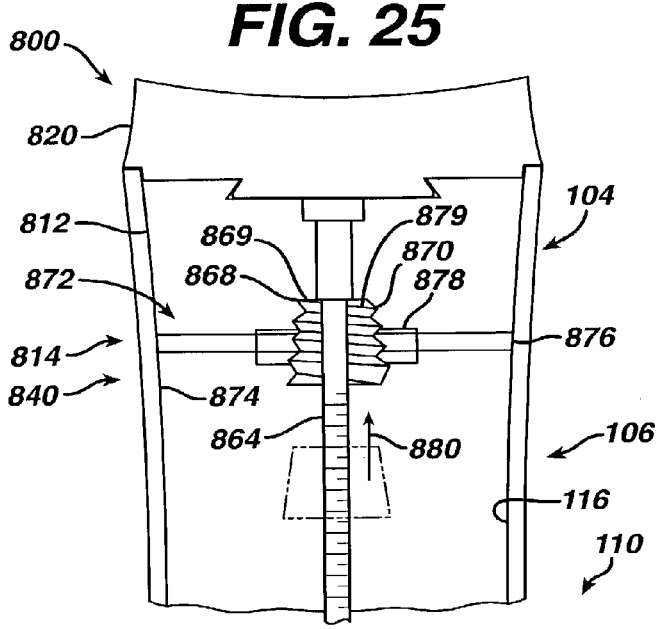
FIG. 25 is a plan view partially in cross section of a wedge type mechanically expandable vault fixed (cementless) glenoid component for use with a prosthetic humeral component for use in performing shoulder joint arthroplasty in accordance with a further embodiment of the present invention.
Figure 26:
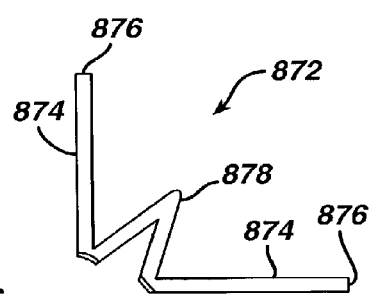
FIG. 26 is a partial top view of the expander of FIG. 25.

Referring now to FIGS. 25 and 26, another embodiment of the present invention is shown as glenoid component 800. Glenoid component 800 is similar to glenoid component 700 of FIG. 24. For example, the glenoid component 800 includes a body 812 similar to the body 712 of the glenoid component 700 of FIG. 24. Further, the glenoid component 800 includes a bearing portion 820 similar to the bearing portion 720 of the glenoid component 700 of FIG. 24. The glenoid component 800 also includes a stem portion 814. The stem portion 814 is similar to the stem portion 714 of the glenoid component 700 in that the stem portion 814 includes an expander 840, similar to the stem portion 714 including an expander 740.

The expander 840 is somewhat different than the expander 740 of the glenoid component 700. The expander 840 includes a screw 864 similar to the screw 764 of the glenoid component 700. The expander 840 also includes a wedge-shaped nut 868. The wedge-shaped nut 868 has a clearance fit to the screw 864. The wedge-shaped nut 868 includes a wedge-shaped outer periphery 870 that is threadably engaged with a spider 872.

The spider 872 includes a series of spaced apart bars 874 which include outer edges 876 that engage inner walls 116 of the glenoid vault 106. The spider 872 further includes an inner band 878 that is threadably engaged with the outer periphery 870 of the wedge-shaped nut 868.

As the screw 864 is rotated to engage the cortical bone of the scapula 110, shoulder 179 of screw 864 engages top 869 of nut 869. Upon contact by the screw 864, the wedge-shaped nut 868 is advanced in the direction of arrow 880, causing the bars 874 to advance outwardly in the direction of arrow 882 until the outer periphery 876 of the bars 874 engage the inner walls 116 of the glenoid vault 106.

The wedge-shaped nut 868 and the spider 872 may be made of any suitable durable material that is compatible with the human body. For example, the spider 872 and the wedge-shaped nut 868 may be made of a titanium alloy, a cobalt chrome alloy, or a stainless steel alloy.

Figure 27:
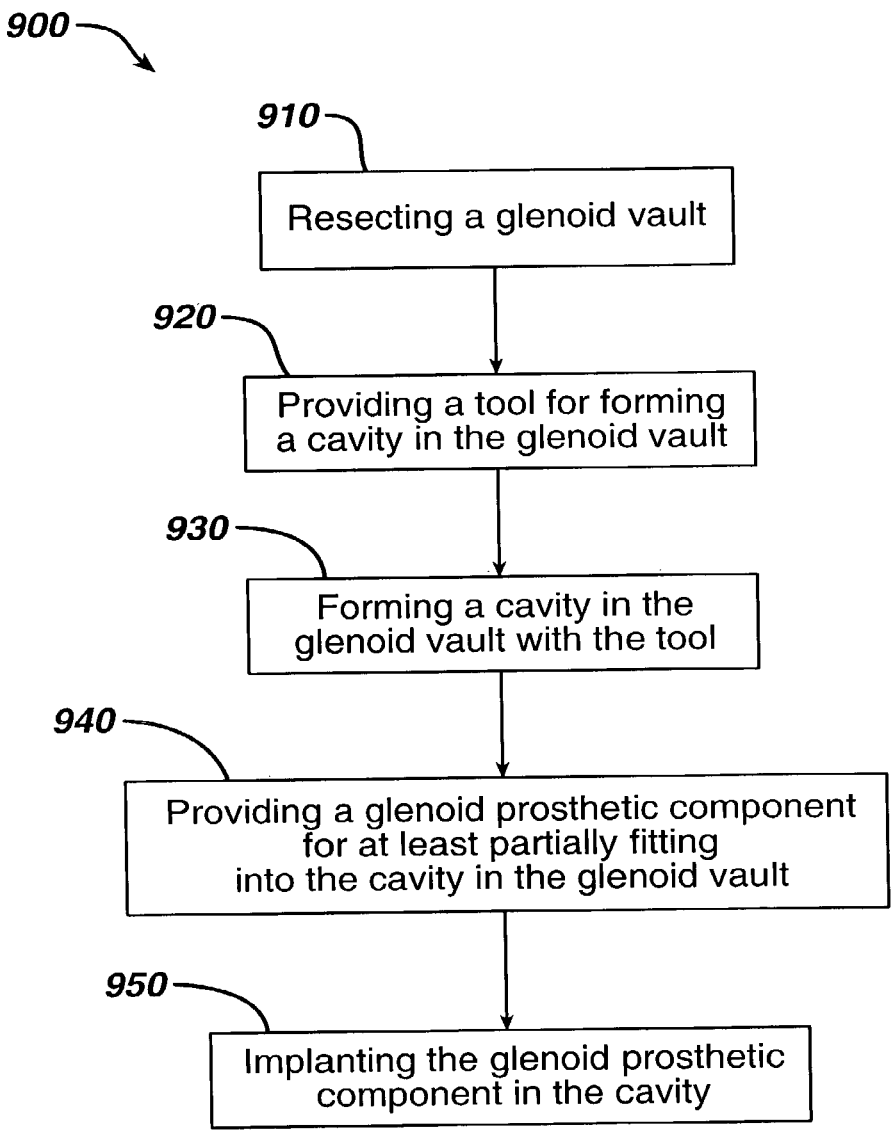
FIG. 27 is a process flow chart for a method of performing shoulder joint arthroplasty according to an embodiment of the present invention.

Referring now to FIG. 27, another embodiment of the present invention is shown as surgical procedure 900. The surgical procedure 900 includes a first step 910 of resecting a glenoid vault. The procedure 900 further includes a second step 920 of providing a tool for forming a cavity in the glenoid vault. The surgical method 900 further includes a third step 930 of forming a cavity in the glenoid vault with a tool. The method 900 further includes a fourth step 940 providing a glenoid prosthetic component for at least partially fitting into the cavity in a glenoid vault. The method 900 further includes a fifth step 950 of implanting the glenoid prosthetic component in the cavity.

Referring now to FIGS. 28 and 29, a template 1010 is shown for preparing the edge 1020 of the cortical bone of the glenoid vault 106. Such a template is particularly useful in connection with the use of the glenoid component 400 of FIG. 18 to prepare edge 473 when a portion of the cortical wall has been lost. The template includes a pilot portion 1030 which mates with the inner wall of the glenoid vault 106 and serves to position the template with respect to the vault 106. The template 1010 also includes a guiding groove 1040 that guides a tool 1050 as it removes bone from the edge 1020 of the glenoid vault 106 to provide a surface for proper support of the glenoid component. The tool 1050 may for example be translated along groove 1040 in the direction of arrow 1060 from first position 1070 as shown in phantom to second position 1080 as shown in solid and then to third position 1090 as shown in phantom.

The template 1010 may be made of any suitable durable material that may be sterilized and may, for example, be made of a metal, for example, cobalt chromium alloy, a titanium alloy or a stainless steel.

Referring now to FIG. 30 the tool 1050 is shown in greater detail. The tool 1050 may include a cutting surface 1100 for cutting the bone. The tool 1050 may also include a stop 1110 for limiting the travel of the tool along its longitudinal axis. The tool 1050 may also include a shank 1120 for connection with a power tool (not shown).

The tool 1050 may be made of any suitable durable material that may be sterilized and may, for example, be made of a metal, for example, a steel alloy, a titanium alloy or a stainless steel. The cutting surface 1100 may be made of a separate material that has improved wear properties such as carbide or diamond.

Although the present invention and its advantages have been described in detail, it should be understood that various changes, substitutions, and alterations can be made therein without departing from the spirit and scope of the present invention as defined by the appended claims.

We claim:

1. A glenoid component for use with a prosthetic humeral component for use in performing shoulder arthroplasty,
    said glenoid component to be fitted at least partially into a generally oval cavity formed in the glenoid vault,
    said glenoid component comprising a body having a stem portion with an oval cross section for inserting at least partially into the generally oval cavity formed in the glenoid vault,
    said stem portion cooperating with an interior wall of the generally oval cavity formed in the glenoid vault when implanted,
    said body having a bearing portion for articulating cooperation with the prosthetic humeral component, wherein said stem portion includes a resilient, integral portion thereof which is conformable to be positionable within the generally oval cavity and expandable upon being positioned in the generally oval cavity to conform to the interior wall of the generally oval cavity.

2. The glenoid component of claim 1, wherein said body comprises a plastic.

3. The glenoid component of claim 2, wherein said body comprises a high molecular weight polyethylene.

4. The glenoid component of claim 1, wherein said body substantially fills the generally oval cavity.

5. The glenoid component of claim 1, further comprising a fastener extending from said body.

6. A glenoid component for use with a prosthetic humeral component for use in performing shoulder arthroplasty,
    said glenoid component to be fitted at least partially into a generally oval cavity formed in the glenoid vault,
    said glenoid component comprising a body having a stem portion with an oval cross section for inserting at least partially into the generally oval cavity formed in the glenoid vault,
    said stem portion cooperating with an interior wall of the generally oval cavity formed in the glenoid vault when implanted,
    said body having a bearing portion for articulating cooperation with the prosthetic humeral component, wherein said stem portion comprises an expander operably connected to said body and at least partially positionable within the generally oval cavity wherein a portion of said expander can be urged against the interior wall of the generally oval cavity.

7. The glenoid component of claim 6, wherein said expander comprises:
    a screw; and
    a tube defining an axial slot thereon, said tube threadably connected to said screw, a portion of said tube being adapted for selective intimate contact with the interior wall of the generally oval cavity.

8. The glenoid component of claim 6, wherein said expander comprises:
    a screw; and
    a member at least partially positionable in the generally oval cavity, said member being threadably connected to said screw, said screw configured to wedgingly threadably expand said member into intimate contact with the interior wall of the generally oval cavity.

9. A glenoid component for use with a prosthetic humeral component, comprising:
    a body having a stem portion comprising an expander operably connected to said body and configured to be positioned at least partially within a cavity formed in a glenoid vault, wherein:

a portion of said expander is configured to be urged against an inner wall of the cavity when the expander is at least partially inserted into the cavity;

said body includes a bearing portion configured for articulating cooperation with the prosthetic humeral component;

said expander includes a screw; and said expander includes a tube defining an axial slot thereon, said tube threadably connected to said screw, a portion of said tube being adapted for selective intimate contact with the inner wall of the cavity.

10. A method of providing shoulder arthroplasty comprising:

providing a tool for forming a cavity in a glenoid vault;

forming a generally oval cavity in the glenoid vault with the tool;

providing a glenoid prosthetic component for at least partially fitting into the generally oval cavity in the glenoid vault;

compressing a resilient lip portion of the glenoid prosthetic component;

inserting the compressed resilient lip portion of the glenoid prosthetic component into the generally oval cavity; and expanding the compressed resilient lip portion within the generally oval cavity.

11. The method of claim 10, wherein the forming the generally oval cavity step comprises forming the generally oval cavity such that the generally oval cavity substantially conforms to the glenoid vault.

12. A method for providing shoulder arthroplasty, comprising:

providing a tool for forming a cavity in a glenoid vault;

forming a generally oval cavity in the glenoid vault with the tool;

providing a glenoid prosthetic component for at least partially fitting into the generally oval cavity in the glenoid vault;

implanting the glenoid prosthetic component in the generally oval cavity;

rotating a threaded member with the glenoid prosthetic component implanted in the generally oval cavity; and forcing an expander against a portion of the cavity by rotation of the threaded member.

13. The method of claim 12, wherein forcing the expander against the portion of the cavity comprises:

bending at least one stave; and forcing a crimped section of the at least one stave against the portion of the cavity.

14. The method of claim 12, wherein forcing the expander against the portion of the cavity comprises:

forcing at least one bar to engage the portion of the cavity using a wedge-shaped nut operably connected to the threaded member.

\* \* \* \* \*